United States Patent [19]
Guiseppi-Elie

[11] Patent Number: 5,312,762
[45] Date of Patent: May 17, 1994

[54] METHOD OF MEASURING AN ANALYTE BY MEASURING ELECTRICAL RESISTANCE OF A POLYMER FILM REACTING WITH THE ANALYTE

[76] Inventor: Anthony Guiseppi-Elie, 1273 Quarry Commons Dr., Yardley, Pa. 19067

[21] Appl. No.: 760,450

[22] Filed: Sep. 13, 1991

Related U.S. Application Data

[63] Continuation-in-part of Ser. No. 322,670, Mar. 13, 1989, abandoned.

[51] Int. Cl.⁵ .................. G01N 27/00; G01N 27/26; C12Q 1/00; C12N 11/04
[52] U.S. Cl. .................. 436/149; 204/403; 435/4; 435/14; 435/25; 435/177; 435/180; 435/182; 435/817; 436/806
[58] Field of Search ............ 435/4, 14, 25, 174, 435/177, 180, 181, 182, 817; 204/403; 436/149, 806

[56] References Cited

U.S. PATENT DOCUMENTS

| | | | |
|---|---|---|---|
| 4,352,884 | 6/1982 | Nakashima et al. | 435/180 |
| 4,371,612 | 2/1983 | Matsumoto et al. | 435/180 X |
| 4,444,892 | 4/1984 | Malmros | 436/528 |
| 4,622,362 | 11/1986 | Rembaum | 435/180 X |
| 4,721,601 | 1/1988 | Wrighton et al. | 422/68 |
| 4,839,017 | 6/1989 | Taniguchi et al. | 435/817 X |

*Primary Examiner*—David M. Naff
*Attorney, Agent, or Firm*—Synnestvedt & Lechner

[57] ABSTRACT

The change in electrical resistance of an electroactive polymer such as polypyrrole, polyaniline or polythiophene when it reacts with an analyte is used to measure the analyte. The open circuit electrical potential of an electroactive polymer film is measured and an electrical potential is applied to the polymer film relative to a reference electrode to oxidize or reduce the polymer film to provide an initial reduced or oxidized state. Then the electrical resistance of the polymer film is measured in the absence of an analyte and the electrical resistance is again measured while the polymer film reacts with the analyte. The analyte concentration is determined from the rte and total amount of electrical resistance change. The electrical resistance is preferably measured by applying a to the polymer film a discontinuous non-perturbating voltage pulse, removing the voltage for a period, making a measurement of open circuit potential and applying a subsequent discontinuous non-perturbating voltage pulse relative to the open-circuit potential. In measuring glucose as the analyte, reaction of glucose with glucose oxidase contained by the polymer film produces hydrogen peroxide which oxidizes the polymer film and makes it more conductive.

3 Claims, 15 Drawing Sheets

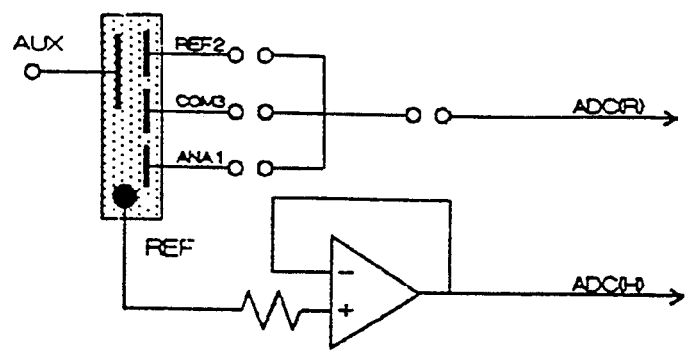
*FIG. 6A* PRE-INITIALIZATION -*Potentiometric Circuit*
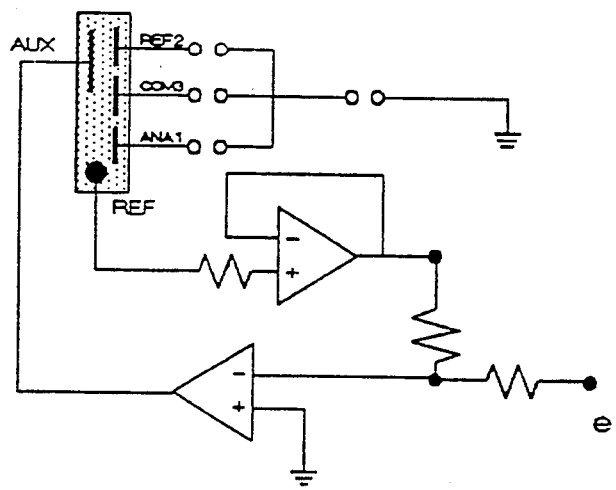
*FIG. 6B* INITIALIZATION - *Potentiostatic Circuit*
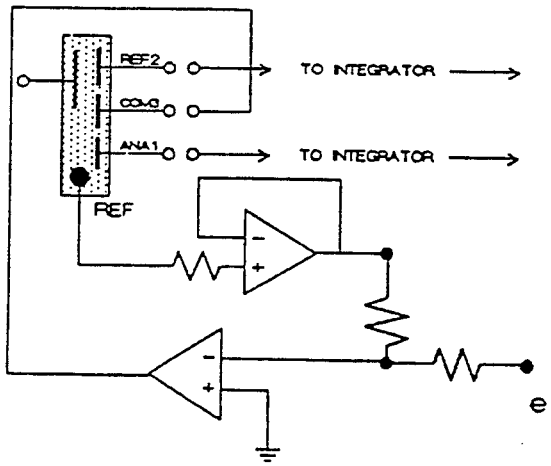
*FIG. 6C* INTERROGATION - *Discontinuous Pulse Chronocoulometry*

SCHEME I

SCHEME III

METHOD OF MEASURING AN ANALYTE BY MEASURING ELECTRICAL RESISTANCE OF A POLYMER FILM REACTING WITH THE ANALYTE

RELATED APPLICATIONS AND CLAIM OF PRIORITY

This application is a continuation-in-part of U.S. application Ser. No. 07/322,670, filed Mar. 13, 1989, now abandoned.

BACKGROUND OF THE INVENTION

For many years, enzyme assays and immunoassays have been successfully used in a wide variety of clinical, veterinary, and bio-analytical laboratory applications. Increasingly, as the availability of monoclonal and polyclonal antibodies has expanded, the range of applications to which these antibodies has extended include environmental monitoring applications (Vanderlaan et. al., 1988). Enzyme and antibody assay technology ahs been used to measure drug abuse, hormones, to monitor therapeutic drugs and to screen for environmental pollutants. These tests are generally simple to use, sensitive, and inexpensive. they are typically, however, colorimetric assays and are at best semi-quantative.

Biosensors offer an alternative format for the performance of established enzyme assays and immunoassays and create new opportunities for the application of established assays to continuous monitoring situations. Biosensors also offer distinct advantages (Taylor, 1987) in being very rapid (sub-second response rates), with condiderably improved limits of detection (typically ppb), are quantitative, and provide electronic outputs that may be integrated into simple data loggers or complex feedback control systems.

Parallel significant advances in microelectronics fabrication technology and biotechnology have created a unique interface of materials science and biology. Biosensors are measurement devices that detect and discriminate among molecules or substances of interest (analytes) through the recognition reactions of biologically active molecules (Lowe, 1985). The biosensor is a microelectronic device or chip, while biorecognition molecules are bioactive proteins. The biosensor measures the concentration of an analyte and produces a proportionate, electrical signal. In biosensors, biologically active molecules provide the needed molecular specificity and confer the ability to detect and discriminate among various substances to be analyzed. Microfabricated solid state devices provide the means for electrical transduction. Together and through their association, these two elements combine to produce an electrically based measurement signal that is the result of the physical chemical changes associated with biorecognition and serve as the raw output data of the biosensor test (Thompson and Krull, 1991).

FIG. 1 schematically illustrates the layout for a typical biosensor instrument. Typically, the biosensor instrument consists of three functionally distinct parts; the biotransducer or biosensor device, the device interrogator and signal processor, and the output device.

Biosensor devices are typically configured as shown in the schematic of FIG. 2. Biosensor devices typically contain two basic parts. The first part is an organic biorecognition layer that contains the biorecognition molecules. The second part is a microdevice which provides the electrical signal and is an electrical or electronically based component. Together, these components form the active element or biotransducer of the biosensor instrument. The biologically active component may be a thin organic film of enzyme, immunochemically active protein, stabilized receptor, a tissue slice, or a cell fragment. This part provides the molecular specificity o recognition of the analyte present in the test sample or process stream. The biologically active part of the transducer converts the analyte into another substance or produces some physical chemical change which can be detected by the electrically or electronically active part of the biotransducer. The electronically or electrically active part of the biotransducer accordingly produces a current or voltage change in response to the appearance of the product of the biological transmutation or conversion reaction. The current or voltage change is an analog signal which may be amplified locally before going on to the second part of the biosensor instrument—the signal processor.

Biosensor devices are integral components of biosensor instruments. The signal processor captures the signal from the biotransducer, may amplify, smooth or perform some mathematical operations on the data, then present it to the next part of the instrument—the output. The output section is responsible for presenting the acquired data in a form suitable for the senses and compatible with other information sources to produce sound and timely decision making by the end user.

This general description of biosensor technology encompasses a wide range of bioanalytical devices, some of which are pH or ion selective electrodes, while others are complicated optical devices.

Electroactive polymer biosensor devices must transmute the chemical potential energy associated with the concentration of an analyte into a proportionate, measurable, electrical signal. The specificity of these electroactive polymer biosensor devices is derived for the biorecognition reactions of immobilized enzymes, enzyme-linked antibody conjugates, and stabilized receptors. Several approaches to the use of electroactive polymers are possible. These are potentiometric, amperometric, chemoresistive, and methods based upon field effect phenomena. In all these methods the electroactive polymer serves as an active, functional, and integral part of the bio-transducer.

Potentiometric biosensor devices derive their responses from the changes in the steady state potential which accompanies the change in redox composition of the electroactive polymer film. This is a direct detection method not requiring the input of externally generated energy. Films may be free standing or supported by ohmic contact to a inert electrode. Changes in extent of oxidation are reflected in changes in the population of polaron o bipoloran states and accompanying counterion ingress. Thus electroactive polymer films therefore serve as ionophore containing membranes of ion-selective electrodes (ISEs). The membrane potential of the electroactive polymer is directly related to some potentiometrically measurable ionic product of the biorecognition reaction (Thompson et al., 1986). In general, all electroactive polymers display som measurable change in steady state or open circuit potential as a function of doping level. This is true over some specified range of redox composition.

Band-gap, p-type semiconducting polymers such as polyacetylene and polypyrrole can change their open-circuit electrode potentials through a maximum of the difference between the mid-gap energy (intrinsic semiconductor) and the conduction band edge, and typically, this change is between the mid-gap energy and the Fermi energy, $E_F-E_{CB}$ (Morrison, 1980). For polyacetylene, the open circuit potential is an invariant 0.45V vs SCE for $CH_x$ compositions above the insulator to semiconductor/metal transition (ca. 4 mol % of dopant per —C=C—unit) (Guiseppi-Elie and Wnek, 1990). Thus the maximum voltage change (over all dopant compositions) associated with these materials is ½ the band gap, $E_g$, or ca. 0.70 V. Direct potentiometric detection of nucleotides co-deposited in electropolymerized polypyrrole has been reported by Shimidzu (1987) and potentiometric measurements of the concentrations of various anions by electropolymerized polypyrrole films have been reported by Dong et. al. (1988). Both these works suggest interesting and unusual behavior of electroactive polypyrrole in potentiometric measurement mode. Since n-type semiconducting band-gap polymers are violently reactive in aqueous environments, their applicability to biosensors is necessarily without consideration.

Redox polymers such as poly(vinylferrocene) and poly(viologen) establish an open circuit potential which reflects the equilibria between oxidized and reduced forms of the redox-active moiety (Lewis et. al., 1984). These devices work by indirectly linking the biorecognition reaction to a change in redox composition of the film. Any signature redox active species which can alter the equilibrium at the polymer modified electrode surface provides a means for biotransduction. These systems all show behavior that can be predicted by the Nernst equation and electrochemical kinetics. Because potentiometric devices based on electroactive polymers are steady state devices they are subject to limitations arising from errors such as interfering ions, non-specific protein binding (Collins and Janata, 1982), surface charge adsorption, and the sensitivity limitations imposed by Band theory and the 59 mV/decade sensitivity of the Nernst equation (Thompson and Krull, 1991).

Amperometric biosensors formed from electroactive polymers ar by far the most common generic approach to biosensors (Janata and Bezegh, 1988). With such devices, two principles dominate: i) redox mediation and ii) electrocatalysis. Redox mediation implies the oxidoreduction of an electroactive species other than the on of interest. Umana and Waller (1986) used the amperometric reduction of iodine ($I_2+2e\rightarrow 2I$) mediated through the $Mo^{IV}$-catalyzed reaction of $H_2O_2$ with iodide ($H_2O_2+2H+2I+2I\rightarrow I_2+2H_2O$) under aerobic conditions.1 Iwakura et. al. (1988) achieved direct redox mediation with ferrocenecarboxylic acid under anaerobic conditions. Similar devices have since also been demonstrated by Caglar and Wnek (1991). In such devices the electroactive polymer functions simply as a retaining matrix for the mediator and is itself not actively involved in transduction. The related works of Heller (1990) and Hale et. al. (1991) use oligomers and polymers of ferrocene-based redox mediators as active participants to transduction (Gorton et. al., 1990). These are true transducer-active polymer films as they both mediate and directly transmute the redox activity of the enzyme to amperometrically discharged current at metallic or carbon paste electrode.

The simplest amperometric biosensors of this type are those based on the discharge of a redox active biproducts of the biochemical transmutation reaction. The early glucose biosensors which amperometrically discharged $H_2O_2$ are of this type (Clark, 1987). There is evidence that electroactive polyaniline modified inert electrodes can electrocatalyze the reduction of ascorbic acid (Hepel, 1990) and hydrogen peroxide (Guiseppi-Elie and Wilson, 1990), both of which are associated with biochemical reactions. Polyaniline modified platinum electrodes have also been reported to electrocatalyze the oxidation of formic acid (Gholamian et. al., 1987). The potential for using electroactive polymer modified electrodes for electrocatalysis in Clark-typ amperometric biosensors is evident but little explored.

Chemoresistive biosensor devices based on electroactive polymer membrane films take advantage of the very large and rapid change in electrical conductivity which accompanies "doping" of the electroactive polymer (Baughman and Shacklette, 1990). The principle of operation in this approach is based on the measurement of biochemically modulated changes in the electronic resistance of the membrane film. The membrane films, fabricated on solid state devices, change their electrical impedance characteristics in response to the biological reactions with which they are associated. Chemoresistive biosensor devices are composed of a fully contiguous membrane film of electroactive polymer fabricated over the interdigit area of Interdigitated Microsensor Electrodes (IMEs) or array microelectrodes. IMEs generally have digit dimensions and separation distances which range from 1 to 20 microns. These dimensions are readily achievable with commonly available microlithography technology. The number of digits and the digit length together define the meander length for the device and this is selected to match the resistance range of the particular electroactive polymer being employed. The short separation distance and long meander length found on IMEs allow the generation of high electric fields with modest voltages while allowing effective work with highly resistive membrane materials. The device sensitivity is provided by the large (up to 12 orders of magnitude) (Frommer and Chance, 1986), dynamic ( ms - $\mu$s response) (Thackeray et. al., 1985) chemoresistance range of chemically sensitive, electroactive polymer membrane films.

Chemoresistive sensor devices based on electroactive polymer films were introduced by Paul et. al. (1985). These redox dependant chemoresistance devices emphasized voltage modulation of the chemoresistive responce. Thackeray et. al. (1985) describe a device based on poly(3-methylthiophene) which illustrates a key strength of this method—The low detection limit ($<10^{-15}$ moles of oxidant) to elicit a response above noise level and the significant amplification possible with proper design of IME and fabrication of the chemically sensitive film (Lofton et. al., 1986). While the foregoing illustrates the general principles of chemoresistance detection the electroactive polymer films used were not conferred with biospecificity and are accordingly not biosensors. Taylor et al. (1988) report receptor-based biosensors using the chemoresistance principle but the polymers used were not electroactive (Taylor, 1989). Malmros et. al. (1987/88) describe a chemoresistance biosensor based on free-standing polyacetylene. This report suggests that the measured chemoresistance response was due primarily to changes in ionic resistance attendant to increases in the extent of wetting of Shirakawa polyacetylene upo doping with aqueous $H_2O_2$ or $I_2$. Chemoresistance biosensors have also been reported by Watson et. al. (1987/88) and Cullen et. al. (1990).

These films are well known to bridge substantial device scale distances (Focke et. al. 1989). Using established methods designed to confer general chemical and biospecificity to these films (Guiseppi-Elie, 1988) and using these devices in a kinetic mode (Karube, 1987) opens up additional possibilities for FETs (Garnier et. al., 1991).

While there have been a large number of prior art biosensors, it would be desirable to have a system and method which can be utilized for the interrogation capture and analysis of chemoresistive sensor responses.

It is thus an object of the present invention to provide a novel analytical method which can be utilized for the interrgogation, capture and analysis of chemoresistive sensor responses.

It is a further object of the present invention to provide novel components which together comprise an electroactive polymer sensor interrogation system.

It is still yet a further object of the present invention to provide chemical and biosensor devices formed from chemically modified and derivatized electroactive polymer films It is still an additional object of the present invention to provide an analytical method for monitoring the time rate of change (kinetic) or extent of change (equilibrium) of the resistance of the electroactive polymer film as it spontaneously reacts with a redox active analyte to which it has been rendered specific These and other objects of the present invention will become apparent from the following summary and detailed description which follow.

SUMMARY OF THE INVENTION

The present invention provides an analytical method for the interrogation, capture, and analysis of the chemoresistive sensor responses of chemical and biosensor devices using the electroactive polymers disclosed and claimed in co-pending U.S. application Ser. No. 07/322,676. Chemoresistive sensor responses are the changes in electrical resistance which result when an electroactive and electrically conducting polymer is made to react with a redox active analyte to which it is rendered specific.

This analytical method may be implemented using components which together comprise an Electroactive Polymer Sensor Interrogation System (hereinafter "EPSIS"). EPSIS comprises an analog electronic instrument with software that ar designed to work together to execute a sequenced series of steps for the extraction of these chemically or biochemically induced, electrically-based sensor responses. A system capable of carrying out the analytical methodology of the present invention is marketed as the Model 240 U EPSIS by AAI/Abtech of Yardley, PA.

The present invention is also directed to chemical and biosensor devices formed from chemically modified and derivatized electroactive polymer films. Previous inventions have described processes and the products resulting from the conferment of chemical and biological specificity to electroactive polymers. The present invention is directed toward the application of these devices to chemical and biosensor applications and to an analytical method for the use of these devices.

In one embodiment of this invention, chemical and biosensor devices are formed by the fabrication of electroactive polymer films on interdigitated microsensor electrodes. Films such a polypyrrole, polyaniline, and polythiophene are grown by electropolymerization from solutions of the corresponding monomer. Films are grown to bridge the interdigit space of the devices. Films may also be cast from solution or colloidal suspension, by dip-coating or spin-coating, where appropriate. Through various chemical modification and derivatization schemes (U.S. Pat. application Ser. No. 322,670) these devices may be functionalized and so conferred with chemical and/or biological specificity. The analytical method of this invention calls for monitoring the time rate of change (kinetic) or extent of change (equilibrium) of the resistance of the electroactive polymer film as it spontaneously reacts with a redox active analyte to which it has been rendered specific.

Key elements of the analytical method are:

(1) The use of an initialization potential which serves to establish a unique redox composition of the film and hence the set the electrical resistivity, open-circuit potential of the device.

(2) The use of very small or non-pertubating net voltage pulses, on the order of 5-25 mV, to interrogate the dynamically changing chemoresistance of the device.

(3) A voltage pulse sequence which floats of disconnects the sensor device during the pulse delay or OFF cycle.

(4) The measurement of the open circuit potential during the pulse delay or OFF cycle and the use of this measured potential to serve as the base potential to which subsequent pulse potentials are added.

The analytical method involves three sequenced phases resulting and an analytically significant result which is related to analyte concentration. These phases are Pre-Initialization, Initialization, and Interrogation. The Interrogation phase comprises three distinct steps to its execution; Voltage Pulse Application, Current Sample, and Device Float. The method of the present invention utilizes a real-time read of the open-circuit potential of the device versus the externally placed reference electrode, such as a $Ag°/AgCl,3MCl^-$. This value of potential becomes an important part of the data record for the particular experiment and is used to qualify the integrity and suitability of the device for the subsequent steps.

The method then superposes an interrogation pulse voltage on the open circuit potential to inquire as to changes in electrical resistivity. In one example, a chemical sensor is formed from the fabrication of a fully contiguous film of electroactive polyaniline over the interdigit space of an interdigitated microsensor electrode (IME). The resulting device is shown to be responsive to hydrogen peroxide and to produce a linear response over the range $10^{-7}$ to $10^{-2}$ M $H_2O_2$ in 0.2M HCl.

In a second example, a mediated chemical sensor is formed from the fabrication of a fully contiguous film of electroactive polypyrrole over the interdigit space of an interdigitated microsensor electrode (IME). The resulting device is shown to be responsive to the mediated concentration of iodine produced by the action of hydrogen peroxide on iodide ion in the presence of $Mo^{(VI)}$. This device is shown to responsive to hydrogen peroxide and to respond linearly over the range $10^{-4}$ M to $10^{-2}$ M $H_2O_2$ in the presence of $10^{-2}$ M $I^-$ and $10^{-3}$ M $Mo^{(VI)}$ in pH 6.0, 0.1M phosphate buffered potassium chloride.

In still yet another example, a glucose biosensor is formed from the fabrication of a fully contiguous film of glucose-functionalized electroactive polypyrrole over the interdigit space of an interdigitated microsensor electrode. The resulting device is made to respond to the concentration of glucose through the biorecognition reaction of glucose oxidase. The device is shown to be responsive to a redox inactive molecule such as glucose through the biotransmutation reaction of glucose oxidase. A kinetic dose/response curve for the chemoresistive glucose biosensor based on the system (PPy/PVAVS/GOx) is shown to be linear for variations in glucose concentration over the range 0.1 to 20 µg/ml in pH 6.0, 0.1M phosphate buffered potassium chloride at 20° C.

BRIEF DESCRIPTION OF THE DRAWINGS

FIG. 6A is a schematic illustration of the potentiometric Pre-Initialization Circuit employed by EPSIS during Phase of operation.

FIG. 6 is a schematic illustration of the potentiostatic Initialization Circuit employed by EPSIS during Phase 2 of operation.

FIG. 6C is a schematic illustration of the Sensor Interrogation or Chemoresistance Measurement Circuit employed by EPSIS during Phase 3 of operation.

DETAILED DESCRIPTION OF THE INVENTION

Figure 1:
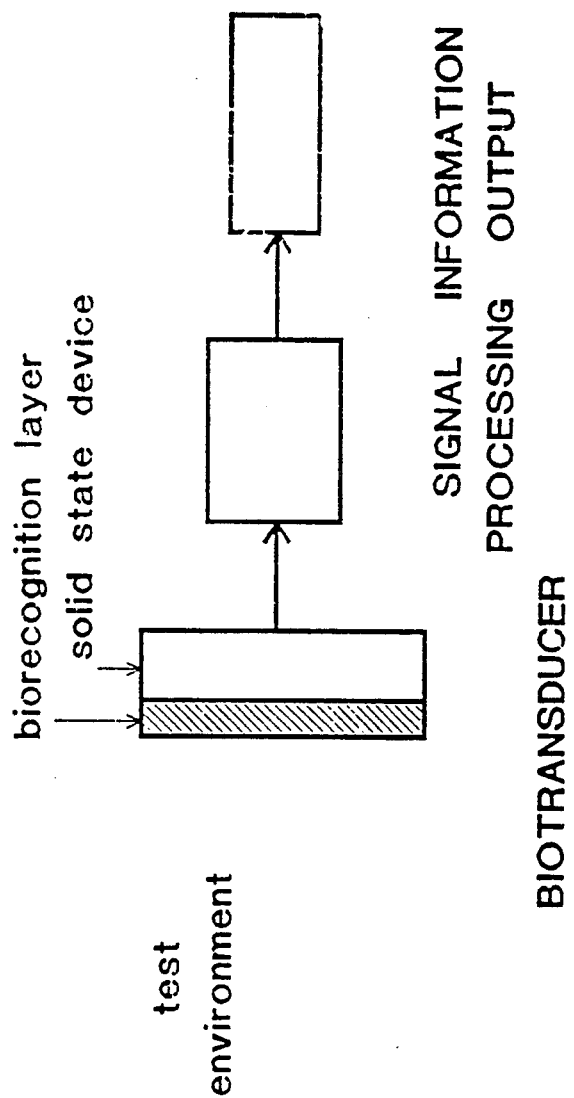
FIG. 1 is an block diagram which illustrates the three basic elements of the archetypical chemical and/or biosensor instrument of the current invention.
Figure 2:
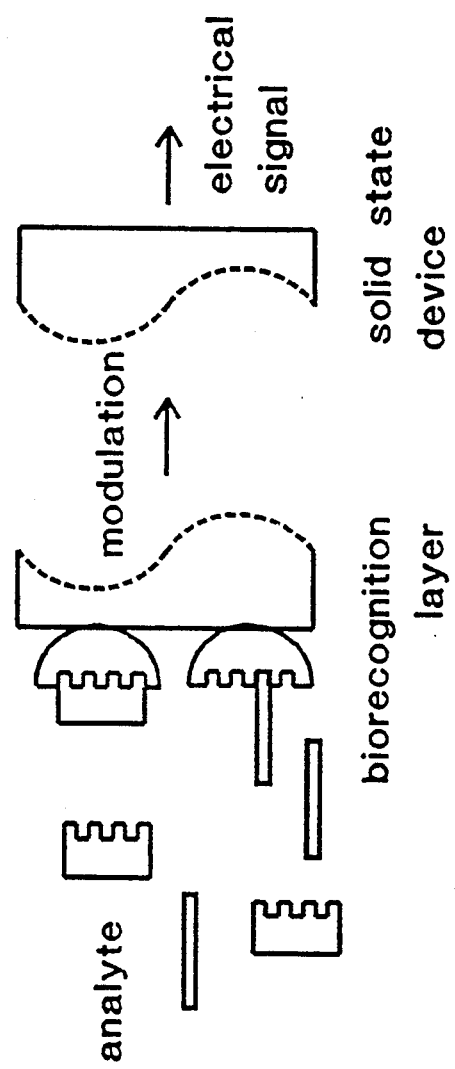
FIG. 2 illustrates the functional elements of the chemical or biosensor device.

The present invention provides a method for obtaining analytically significant responses from chemical and biosensor devices based on electroactive polymer films. In the analytical method of the present invention, the use of an initialization potential to fix the starting redox composition, and consequently also fix the ionic and electronic resistivity and the electrode potential of the device, the use of non-pertubating voltage pulses for interrogation, the use of a float or disconnect period between the application of voltage pulses, the measurement and update of the device potential during each float period, and the use of this measured float potential to establish the new pulse potential for subsequent pulse application are utilized.

The initialization potential is potentiostatically applied for a period sufficiant to fix the redox composition of the polyme film. This potential may be anodic or cathodic and may fix the composition to be predominantly oxidized and conducting or predominantly reduced and non-conducting. Typically, the potential is chosen to reduce the polymer film, render it non-conducting or resisitive, and fix its redox composition to be predomninantly reduced. It is understood by those skilled in the art, that for this class of material such initialization also fixes the color of the device film as well as the geometric dimensions of the film. The length of time required for initialization depends upon the nature of the film, the thickness of the film, the total active or exposed area of the film in contact with the electrolyte, and the nature of the electrolyte. The initialization period is typically 8 to 30 secs and may be 1 sec to 3 mins. Alternatively, initialuization may be made to proceed until a limiting background current is achieved or a particular threshold of current achieved.

Immediately subsequent to initialization, an interrogating voltage pulse is applied to the device. This voltage pulseis intended to reveal the electrical conductivity of the electroactive polymer film. This pulse must therefore be non-pertubing to the film and should not itself serve to alter the redox composition or conductivity of the film. The voltage pulse may be in the range $+$or $-5$ to 25 mV and may be 1 to 100ms duration and is typically 10mV for a 50ms duration. Larger voltages may be applied and for longer durations. The resulting current indicates the electrical conductivity of the film bearing device and ma be mathematically converted to absolute or normalized resistivity or conductivity.

At the end of the interrogating voltage pulse period the device is disconnected form the voltage source, is permitted to electrically float, and to spontaneously react with the analyte species of its test environment. During this float period the device responds with a change in redox composition, ionic and electrical conductivity, and electrode potential. The float period is typically ten times the pulse period and may be 10ms to 1000ms duration and is typically 500ms. During the float period, the open circuit or poise potential of the individual electrodes of the device are measured versus the externally place $Ag/AgCl,3MCl^-$ reference electrode. No current is drawn or voltage applied during this measurement. The measured float potential is used as the base potential value for the application of the subsequent interrogation voltage pulse.

The 10 mV pulse potential is added to the float potential such that the subsequentially applied potential differs from th device open circuit potential by only the value of the interrogation pulse potential. As an example, if the measured open circuit potential of the device during the float period is found to be 345 mV vs the Ag/AgCl,3MCl− reference electrode and the desired pulse voltage is 10 mV, then the subsequent voltage pulse applied to the device is 355 mV vs Ag/AgCl,3MCl− for a net voltage applied of 10 mV.

Chemical and biosensor devices are formed from electroactive polymer films of polyaniline and polypyrrole and are shown to produce analytically significant results. This invention is further illustrated by reference to the following non-limiting examples. These examples serve to illustrate the wide utility of the method as it is successfully applied to chemical as well as biosensors.

INTERDIGITATED MICROSENSOR ELECTRODES—IME Devices

Figure 3A:
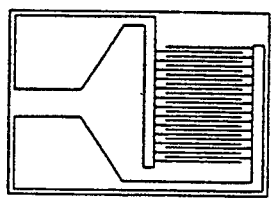
FIG. 3 illustrates the various designs for the chemical and biosensor devices formed from Electroactive Polymer Microsensor Electrode
Figure 3B:
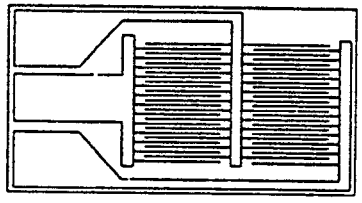
Figure 3C:
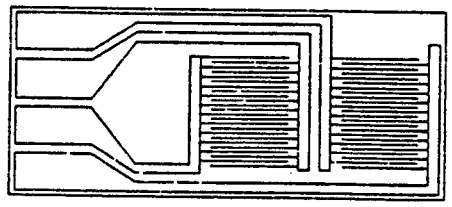

Interdigitated Microsensor Electrodes (IMEs) are inert, array microelectrodes designed for the simultaneous interrogation of the electrical, electrochemical, and optical properties of thin polymer films and coatings. Microfabricated from magnetron sputtered gold over and an adhesion metal of chromium or titanium, on an insulating ceramic substrate of glass, quartz, lithium niobate or passivated silicon these devices were developed for application to chemoresistive biosensor assays. The IME devices are inert, rugged, durable and versatile and occur in three different electrode configurations shown in FIG. 3; Monolith (M), Combined Differential (CD), and Full Differential (FD). These IMEs consist of 50 digit or finger pairs. Each digit is 0.4985 cm long and 15 $\mu$m wide and is separated by 15 $\mu$m spaces on a chip which is typically 1.0 cm(W)$\times$1.5 cm(L)$\times$0.05 cm(T) with a total exposed metal area of 0.569 cm$^2$.

ELECTROACTIVE POLYMER MICROSENSOR ELECTRODES—EPME Devices

Electroactive Polymer Microsensor Devices (EPMEs) serve as the underlying transducers for the fabrication of biosensor devices. Transducer-Active Films based on polyaniline, polypyrrole, polythiophene, or other electroactive polymer is fabricated as a fully contiguous film over the device. Film fabrication occurs by electropolymerization of aniline, pyrrole or thiophene monomer from electrolyte solutions. The electropolymerization medium contains polymeric counter-anions and supporting electrolyte and may contain surfactants, levelling agents, bioactive proteins, catalysts and other agents directed at enhancing the performance or properties of the film. Electropolymerization is carried out directly at IME devices resulting in EPME devices.

The Electroactive Polymer Sensor Interrogration System (EPSIS)

Electroactive polymer sensor interrogation was accomplished with the EPSIS 240 U system. EPSIS is a sensor interrogation, data capture, and analysis instrumentation package for the development of biosensor assays using Biospecific EPME devices. The EPSIS 240 U unit is commercially available through AAI\Abtech, Inc., 1273 Quarry Commons Drive, Yardley, PA 19067. Wnile the present analytical methodology was carried out using the AAI/Abtech EPSIS 240 U system, it is to be appreciated that the focus of the present invention is on the analytical methodology and that this methodology may be performed by a wide variety of apparatus.

Figure 4:
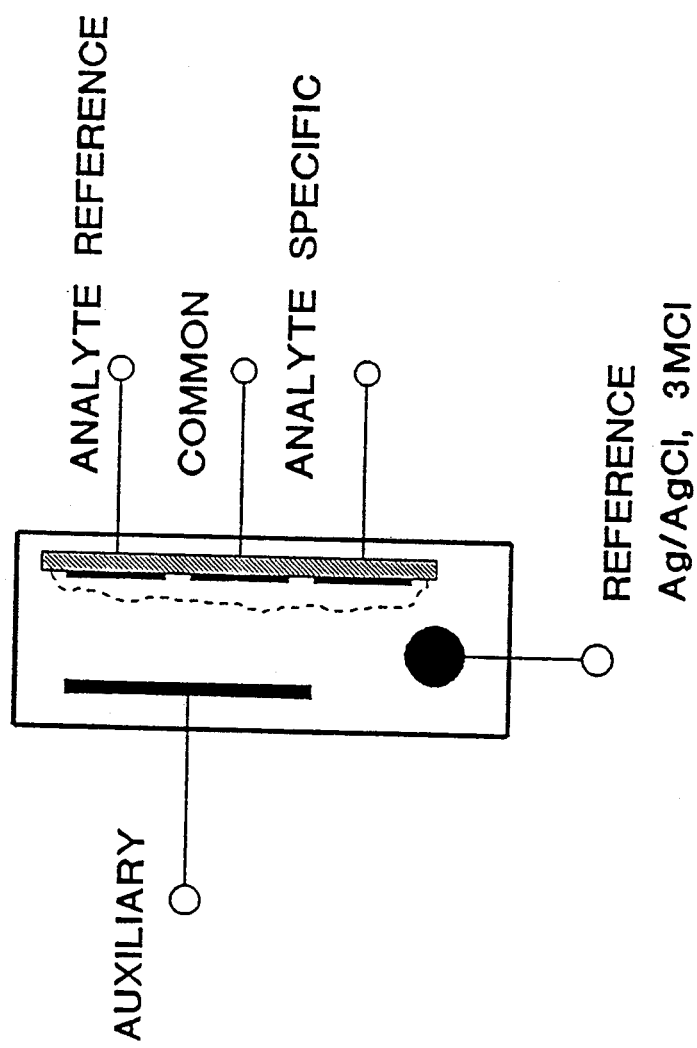
FIG. 4 is a section view illustrating the various electrode connections to the chemical and biosensor cell.

EPSIS uses the Biospecific EPME device in a biosensor cell comprising a platinum counter electrode and an externally placed miniature Ag/AgCl/3MCl− reference electrode. Both the counter electrode and the reference electrode functions may be fabricated on the same EPME device chip which carries the biospecific agents. For the purpose of illustration and for experiments performed here, these are shown as separate electrodes in the biosensor cell arrangement illustrated in FIG. 4.

Figure 5:
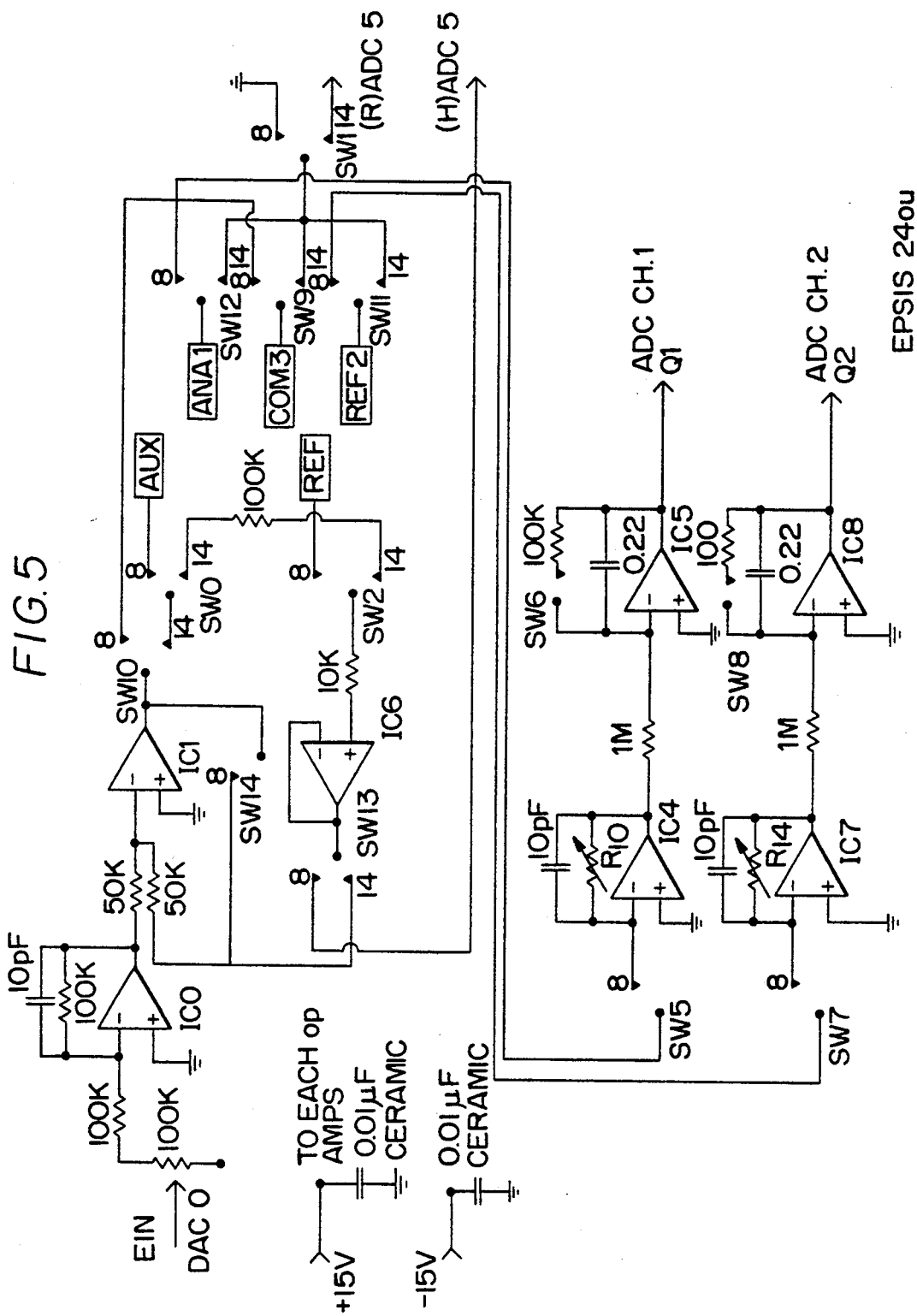
FIG. 5 is a schematic of the Electroactive Polymer Sensor Interrogation System which may be utilized to perform the analytic method of the present invention.

EPSIS instrumentation consists of the EPSIS 240 U sensor interrogator and EPSISOFT TM software installed on a PC XT computer outfitted with a 12 bit AD card. A scematic represenation is shown in FIG. 5. The EPSIS 240 U consists of a potentiometric circuit, a potentiostatic circuit and a chemoresistance interrogation circuit illustrated in FIGS. 6A–6C. These instrument functions are integrated into a sensor interrogation system designed to reveal the chemoresistance dynamics of electroactive polymer films as they respond to biologically modulated changes in electrical conductivity.

Figure 7:
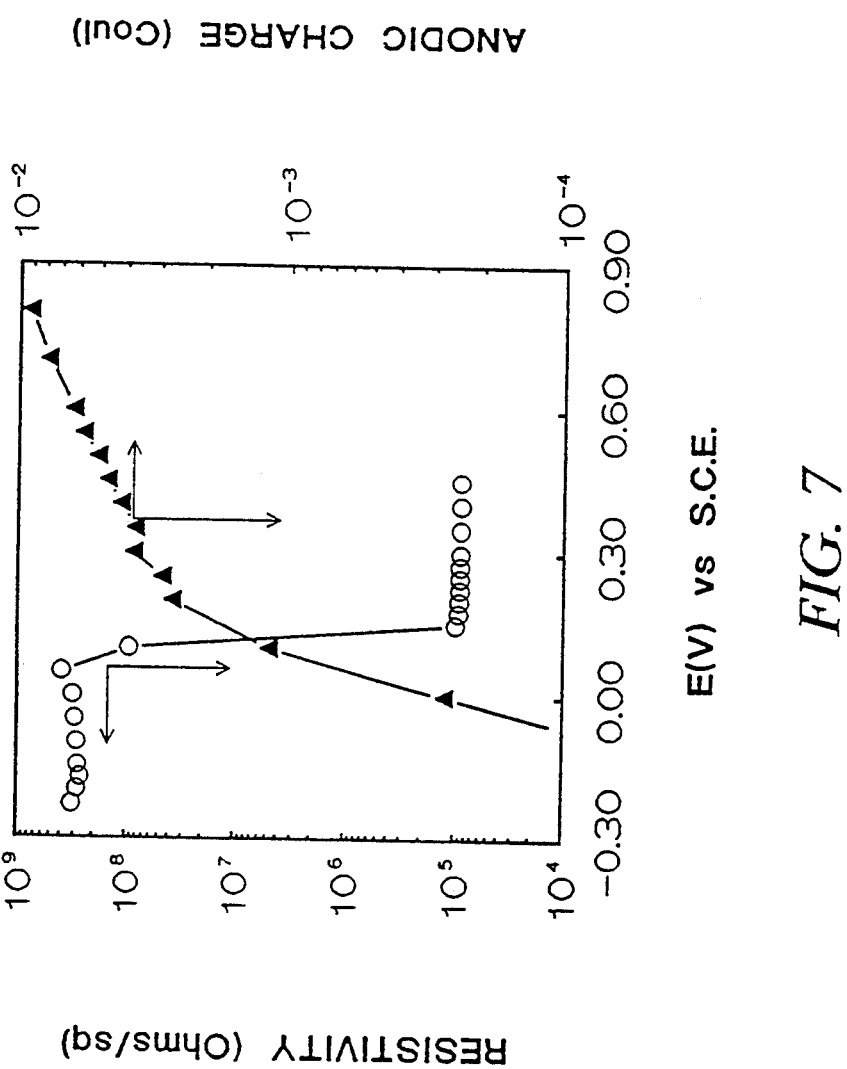
FIG. 7 is a graph showing the electrical resistivity and the anodic charge capacity (measured by potential step coulometry) of polyaniline films as a function of the impressed potential vs SCE in 0.2M HCl.
Figure 8:
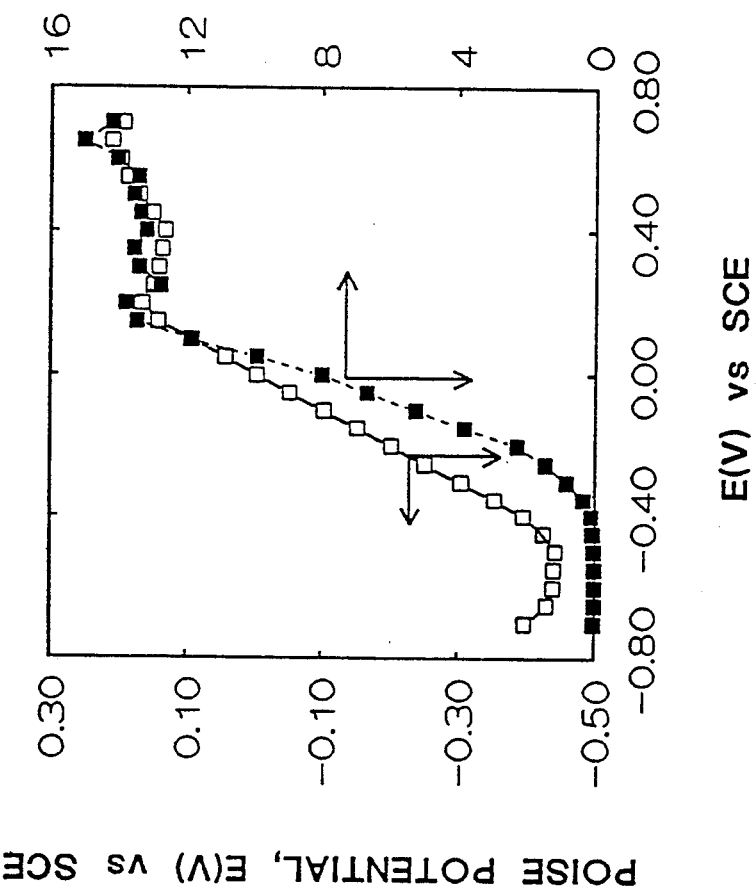
FIG. 8 is a graph showing the electrical resistivity (expressed as coulombs of charge) and the poise potential in V v SCE versus the externally impressed potential vs SCE in pH 6.0. 0.1 M phosphate buffered potassium chloride.

Because the biospecific, transducer-active films display very dramatic changes in electrical impedance as a function of extent of oxidoreducton, the biospecific EPME device may be used as a highly sensitive biotransducer. FIG. 7, as an example, illustrates the changes in the electrical resistivity and the anodic oxidative capacity of electroactive polyaniline films as a function of electrode potential in 0.20M HCl. Similar results are shown for polypyrrole (Chidsey and Murray, 1986). The method senses the kinetic and equilibrium changes in chemoresistance of these devices as the resistivity of the device is modulated by reaction with the signature products of the biorecognition molecules with which the area derivatized.

The general procedure for the interrogation of the electroactive polymer microsensor devices (EPMEs), interdigitated microsensor electrodes (IMEs) or other chemoresistive device based on electroactive polymer films, involves three separate, sequenced phases that are integrated into a sensor analysis scheme. These phases are listed below.
1. Pre-Initialization Phase
2 Initialization Phase
3. Interrogation The three phases, executed in sequence, represent a single complete cycle for the successful extraction of raw sensor response data. The raw data extracted should be relatable to the desired measurement objective, i.e. the activities (chemical potential) of analytes to which th device is sensitive. Subsequent data reduction, analysis, and presentation follows these two phases.
Pre-Initialization Phase: Initially, a real-time read of the open circuit potential of the device versus a suitable externally placed reference electrode such as a Ag°\AgCl, 3MCl−.

This potential serves to qualify the device for subsequent initialization and interrogation and therefore serves as a diagnostic tool as to the suitability of your device for further experimentation.

During pre-initialization all two, three or four electrodes of the microsensor device are internally shorted to serve as the common input for the potentiometric circuit shown on this is illustrated in FIG. 6A. The potentiometric circuit is a high input impedance FET operatinal amplifier.

Electrode potential, the initialization potential, to the internally shorted microsensor device. All of the two, three or four electrodes of the microsensor device are simultaneously polarized to this potential. The device is maintained at this fixed potential, relative to the externally placed reference electrode for the user specified length of time, the Initialization Period.

Initialization conditions or reconditions the microsensor device to an initial or starting extent of oxidation or reduction from which accurate sensor response measurements may be made during the subsequent interrogation phase. During initialization, the chemically sensitive polymer film may be partially or completely oxidized or reduced. This process, in effect, standardizes the starting electrical conductivity of the chemoresistive film. The instantaneously measured ope circuit rest potential of the device following initialization is hypothetically the same as the initialization potential. Initialization therefore serves to establish a common precondition which is the same for each device, the same from one device to another, and the same from one measurement to another with the same device.

During initialization all two, three or four electrodes of the microsensor device remain temporarily shorted as EPSIS electronically switches from a potentiometric to a potentiostatic mode and the initialization potential is app ied. This configuration is illustrated in FIG. 6B. The applied initialization potential is referenced to a suitable, externally placed reference electrode, such as SCE or Ag Ag°\AgCl. The initialization current is carried by a suitable inert, counter or auxiliary electrode. The VALUE of potential used is dependent upon the analyte to be measured, the background environment or matrix of this analyte, the redox characteristics of the chemically sensitive film of the device, and the extent of oxidation/reduction desired for this conditioning. Initialization is a redox process that involves facile electron transfer and results in a standardized chemoresistive film.

The chemoresistive microsensor device is then as to its dynamically changing state of electrical conductivity (chemoresistance). This it achieved by applying a pulsed DC voltage between the individual electrodes of the microsensor device and sampling the resulting current.

Interrogation probes the device for its electrically based response to the externally derived chemical or biological stimuli. The stimulus is in all cases the chemical potential of the analyte. The device response is a change in its electrically based material property, modulated by the chemical potential of the analyte under test. Interrogation reveals raw data on the electrical condition of the device and in particular is concerned with either the extent of variation of the resistive property of the device from its initialization condition or with the time rate of variation of the resistance of the device away from its initialization condition.

During interrogation as shown in FIG. 6C, the two, three or four leads of the microsensor device are temporarily disconnected. The now independent leads give rise to two separate interrogation circuits that share a common input electrode, COM(1,2)3 (in a bridge configuration). In this electrode configuration, the pulsed DC voltage is applied between COM(1,2)3 and ANA1 and simultaneously between COM(1,2)3 and REF2. The microsensor device portion of the interrogation circuit is treated as a complex impedance from which we desire to know only of the equivalent DC resistance.

The desired mode of interrogation is a pulsed square wave technique. During interrogation a discontinuous pulse.voltage train is applied between the common electrode, COM (1,2)3, and ANA1 and REF2. The voltage pulse should be small and non-perturbing (approx. 25 mV). The voltage pulse is applied relative to the open circuit potential of the device and is superposed on the open circuit potential. The duty cycle is established such that the time between pulses is long compared to the applied pulse width, typically 10 times.

The pulse that is applied may be positive or negative, but should not be an alternating positive and negative value. The duty cycle of the pulse must be sufficient to allow for the dissipation of any Faradaic or capacitative charging in the device.

During the voltage pulse delay period of the interrogation cycle, the electrodes of the microsensor device are briefly reconnected to provide a measurement of the open circuit or rest potential. The electrode configuration is the same as the connect or potentiometric mode of the pre-initialization phase. This open circuit potential serves as the referenced basis for the subsesquent voltage pulse. The open circuit potential of the device is measured at the end of each pulse delay. This potential then serves as the referenced basis for the subsequent pulse. This cycle is repeated again and again for the number of cycles selected for interrogation and until the end of the experiment. The resulting interrogation current is sampled over a fixed period of the applied voltage pulse. Current sampling in this manner negates the contribution of any current transients that may result from Faradic charging processes or other polarization processes in the device or in the background electrolyte. The sampled current is directed to a current-to-voltage converter, then integrated and presented as coulombs of charge over the time base.

The external sensitivity setting yo select will be determined by a number of experimental variables; the thickness of any chemoresistive film fabricated upon the sensor device, the concentration of electroactive species in the vicinity of the microsensor device, the active device area (and to some extent, its shape), the pre-integration delay and the integration period. The selection of too large an electrode area or too long an integration period—both of which may lead to amplifier saturation and to unusable output signal—are common experimental errors.

EXAMPLE 2

Electropolymerization of aniline (An) and cyclic voltammetric characterization of polyaniline (PAn) films were carried out using an EG&G PAR 173 Potentiostat/Galvanostat outfitted with a PAR 179 Digital Coulometer. Where needed, potentiodynamic sweeps were accomplished by interfacing the PAR 173 to a PAR 175 Universal Programmer. Cyclic voltammograms were recorded on an Esterline Angus XYY' 540 Recorder. Aniline ($C_6H_5NH_2$) was supplied by Aldrich and used after distillation under reduced nitrogen pressure. The solvents acetone and 2-propanol were supplied by Aldrich and used as supplied. Ominsolve water was supplied by VWR Scientific. Hydrogen peroxide was supplied by Sigma. Phosphate (0.1M) buffered potassium chloride (pH 7.2) solutions were prepared according to procedures of the Handbook of Physics and Chemistry. Pt foil electrodes were fabricated in these laboratories and saturated calomel electrodes (SCE) wer supplied by Fisher.

Electropolymerization was done at Interdigitated Microsensor Electrodes (IMEs) Model 1550-CD-P. The IME 1550-CD-P devices were cleaned in a Branson 1200 Ultrasonic Cleaner by sequential washing —first in acetone, followed by 2-propanol and finally in Omnisolve triply distilled water. Chemically cleaned microsensor devices were then made the working electrode in a three electrode electrochemical cell in which a similarly cleaned Pt foil electrode served as the counter electrode and an SCE served as the reference electrode. Cathodic cleaning of the IME 1550-CD-P was carried out in pH 7.2 phosphate buffered potassium chloride by cycling between −2.0V and −1.2V vs SCE for eight minutes. To promote adhesion of the electroactive polyniline film, the cathodically cleaned device was subsequently immersed for 30 minutes in a freshly prepared 0.2mg/ml solution of 4-aminothiophenol (Aldrich) in Omnisolve water followed by rinsing in Omnisolve water. Polyaniline films were fabricated by electropolymerization from aqueous solutions of aniline (An) monomer in the presence of HCl. Films were fabricated potentiostatically at potentials of 0.65V–0.8 V and typically was 0.65 V vs SCE or potentiodynamically over the range −0.2 to +0.65 V vs SCE at 50 mV/sec.

Electropolymerization solutions were typically 1M aniline in 0.2M HCl in triply distilled water. The result in all cases was a fully contiguous film of electroactive polyaniline fabricatd over the interdigit areas and adhered to a 1550-CD-P EPME device.

EXAMPLE 3

Electropolymerization of pyrrole (Py) and cyclic voltammetric characterization of polypyrrole (PPy) films were carried out using an EG&G PAR 173 Potentiostat/Galvanostat outfitted with a PAR 179 Digital Coulometer. Where needed, potentiodynamic sweeps were accomplished by interfacing the PAR 173 to a PAR 175 Universal Programmer. Cyclic voltammograms were recorded on an Esterline Angus XYY' 540 Recorder. Pyrrole ($C_4H_4NH$), potassium iodide, ammonium molybdate(VI) tetrahydrate, and the solvents; acetone, 2-propanol, were supplied by Aldrich and used as supplied. Hydrogen peroxide was supplied by Sigma. Phosphate (0.1M) buffered potassium chloride (pH 6.0) solutions were prepared in the standard way. Pt foil electrodes were fabricated in these laboratories and saturated calomel electrodes (SCE) were supplied by Fisher. Electropolymerization was done at Interdigitated Microsensor Electrodes (IMEs) Model 1550-CD-P. The IME 1550-CD-P devices were cleaned in a Branson 1200 Ultrasonic Cleaner by sequential washing —first in acetone, followed by 2-propanol and finally in Omnisolve triply distilled water. Chemically cleaned microsensor devices were then made the working electrode in a three electrode electrochemical cell in which a similarly cleaned Pt foil electrode served as the counter electrode and an SCE served as the reference electrode. Cathodic cleaning of the IME 1550-CD-P was carried out in pH 7.2 phosphate buffered potassium chloride by cycling between −2.0V and −1.2V vs SCE for eight minutes.

To promote adhesion of the electroactive polypyrrole films, the cathodically cleaned device was subsequently immersed for ca. 1 hr in a freshly prepared 100μg/ml solution of potassium p-toluenethiosulfonate (Aldrich) in Omnisolve water followed by rinsing in Omnisolve water. Polypyrrole films were fabricated by electropolymerization from aqueous solutions of pyrrole (Py) monomer in the presence of poly(vinylacetamide-vinylsulphonate, 60:40) (PVAVS) at potentials of 0.65V–0.8 V vs SCE. Electropolymerization solutions were typically $10^{-2}$M pyrrole in triply distilled water. The poly(vinylacetamide-vinylsulphonate 60:40) was of MW 20,000–80,000 supplied by Polysciences and was prepared to a final concentration which varied from $10^{-3}$ to $10^{-2}$M in repeat units. Where needed, ammonium molybdate hexahydrate was also added to the electropolymerization solution to produce a final concentration which was $10^{-3}$M $Mo^{(VI)}$. The result in all cases was a fully contiguous electroactive polymer blend of PPy/PVAVS fabricated over the interdigit areas and adhered to a 1550-CD-P EPME device.

EXAMPLE 4

The EPME device is conferred with appropriate biospecificity for application as a biosensor. By conferring biological specificity to the device, the materials property change of the transducer-active polymer film may be linked directly or indirectly to the concentrations of specific analytes in the vicinity of the device. A contemporary problem in biosensor R&D is the development of approaches, methods and techniques for conferring biospecificity of response to these chemically sensitive films. Approaches based on the use of macrocycles, permselective membranes, electrochemical pre-concentration techniques are used to confer general chemical specificity. Approaches based on the use of enzymes, enzyme-linked antibodies, and stabilized receptors give rise to a wide range of possible chemoresistive biosensors. The conferment of biospecificity to the transducer action of these transducer-active polymer films is readily achieved by derivatization. Derivatization methods may based on adsorption, occlusion, codeposition and specific immobilization of bioactive molecules to these films. Methods for the surface modification, functionalization, and derivatization by specific immobilization of biologically active molecules to the surfaces of transducer-active polymers are easily developed and applied by the methods set forth in U.S. application Ser. No. 322,670 incorporated herein by reference.

Biospecificity was conferred to electroactive polypyrrole (PPy) films by electropolymerization of pyrrole (Py) monomer in the presence of the enzyme glucose oxidase (GOx) and the polymer poly(vinylacetamide-vinylsulphonate, 60:40) (PVAVS) at potentials of 0.65V–0.8 V vs SCE. Electropolymerization solutions were typically $10^{-2}$M pyrrole in triply distilled water. The GOx was *Aspergillus niger* Type VII-S of 129K units/g activity (Sigma) prepared to a final concentration of 1mg/ml. The poly(vinyl acetamide-vinylsulphonate 60:40) was of MW 20,000–80,000 supplied by Polysciences and was prepared to a final concentration which varied from $10^{-3}$ to $10^{-2}$M in repeat units. Where needed, ammonium molybdate hexahydrate was also added to the electropolymerization solution to produce a final concentration which was $10^{-3}$M $Mo^{(VI)}$. The result in all cases was a fully contiguous electroactive polymer blend of PPy/PVAVS/GOx fabricated over the interdigit areas and adhered to a 1550-CD-P EPME device.

EXAMPLE 5

General Chemical Sensor Response

Figure 9:
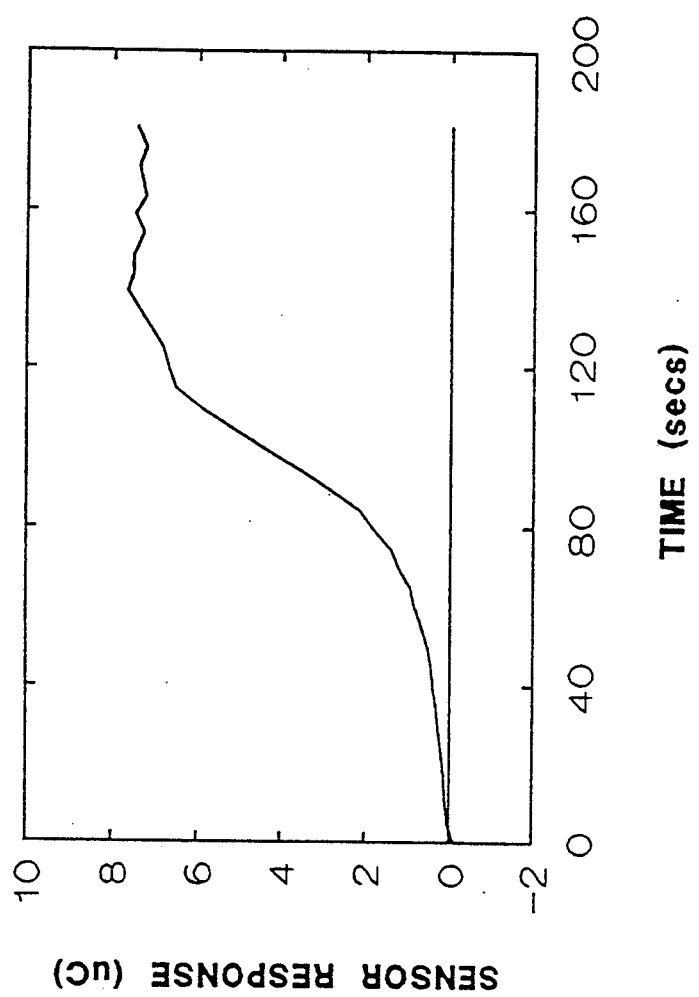
FIG. 9 is a graph showing a typical differential chemoresistive response of a polyaniline-based sensor to 1 mM hydrogen peroxide in 0.2M HCl relative to its response in 0.2M HCl.
Figure 10:
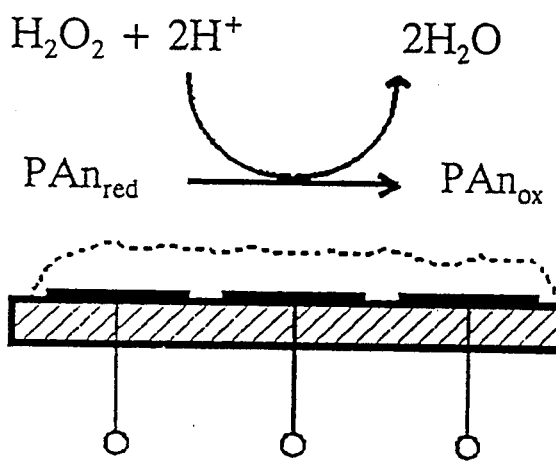
FIG. 10 is an illustration of a typical chemical sensor reaction, SCHEME 1.

Polyaniline-based sensor devices prepared according to Example 2 were evaluated for their chemically induced sensor responses using the EPSIS system Described in Example 1. The three step interrogation phase of EPSIS is repeated for a user-selected number of pulse cycles applied in sequence. The integrated device current for each pulse is then plotted directly to the data display area of the EPSISOFT Main Menu Screen and is shown as microcoulombs of charge versus interrogation time in seconds. A typical chemoresistive sensor response of a polyaniline membrane film to 1 mM $H_2O_2$ in 0.2M HCl along with a similar blank response (0.2M HCl) is displayed in FIG. 9. The response is for the PAn film initialized at $-100$ mV vs Ag/AgCl,3MCl$^-$ for 30 sec and interrogated at 10 mV pulse potential with a pulse width of 50ms and rest period of 500 ms. The Figure shows the response obtained over 164 such three-step, pulse cycles or for a total of 90.7 sec. Typically there is a brief induction period followed by a sharp rise in the chemoresistance of the film. Exploration (in 50 mV increments) of various initialization potentials, from the open circuit potential of the mixed emeraldine base (0.43 V vs Ag/AgCl,3MCl$^-$) down to the fully reduced leucoemeraldine base ($-0.30$V vs Ag/AgCl,3MCl$^-$), produced the largest kinetic response for initializations at $-0.1$V vs Ag/AgCl,3MCl$^-$. Initialization at $-100$ mV vs Ag/AgCl,3MCl$^-$ reduces the PAn film and sets its equilibrium redox composition and attendant electrical conductivity according to FIG. 7. The time rate of change of the electrical conductivity of PAn film appears to be largest from this composition. Removal of this potential allows the film to spontaneously react with the hydrogen peroxide in its immediate environment as shown in FIG. 10, Scheme I. Subsequent immediate three-step, DC pulse interrogation reveals the concomitant changes in electrical conductivity of the film as it reacts with hydrogen peroxide and modulates its properties.

At the end of this interrogation cycle the membrane film may be re-initialized and a similar response reproducibly obtained. Kinetic response data is derived for the initial rate of change of the chemoresistive response. Ideally, this is the initial slope of the response curve or it may be the amount of change after a specified period of interrogation time. The latter approach is used to analyze the kinetic responses of PAn films to various concentrations of $H_2O_2$ FIG. 9 shows the sensor calibration curve of differential response rate obtained for concentrations over the range $10.^{-7}$ to $10^{-2}$M $H_2O_2$ in 0.2M HCl.

The chemoresistive PAn devices are seen to be linear over the range $10^{-7}$ to $10^{-2}$M $H_2O_2$ in 0.2M HCl with good sensitivity and a detection limit which is below 10; M $H_2O_2$. The stability of these devices is of paramount importance if they are to be used commercially and in continuous monitoring applications. Preliminary evidence from cyclic voltammetric characterization of PAn films suggests that the device performance may be altered by continuous exposure to high concentrations ($>10^{-2}$M) of hydrogen peroxide.

EXAMPLE 6

Figure 12:
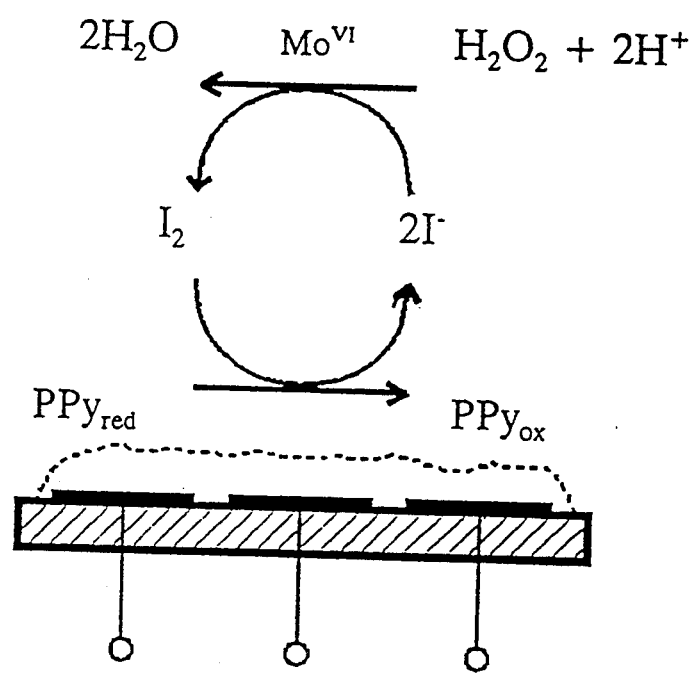
FIG. 12 is an illustration of a typical mediated chemical sensor reaction, SCHEME 2.
Figure 13:
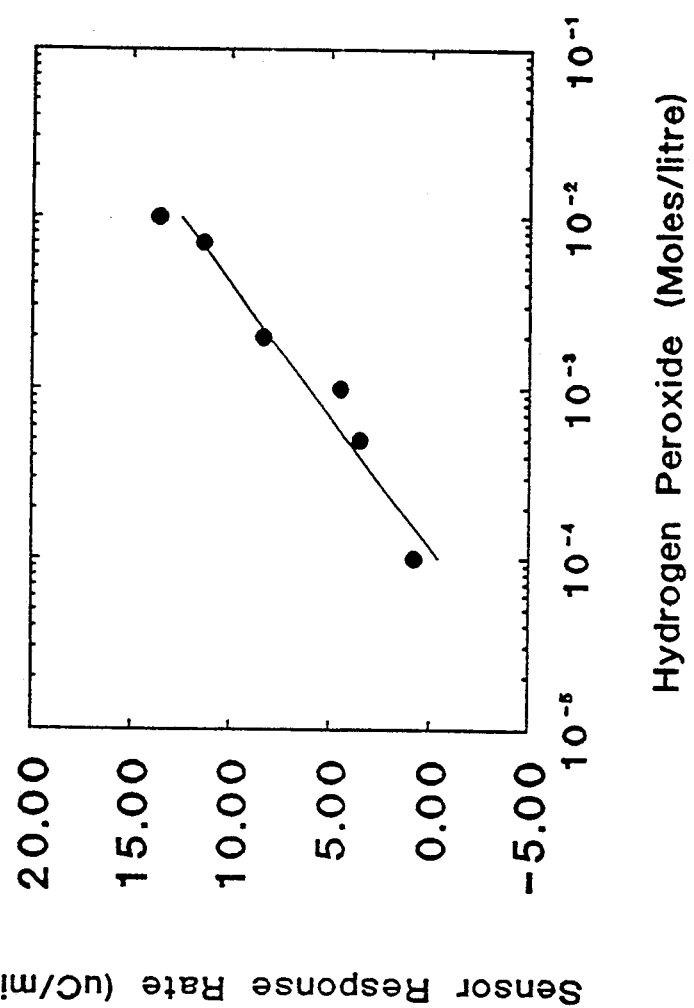
FIG. 13 is a graph showing the kinetic chemoresistive responses of a polypyrrole-based sensor (PPy/PVAVS) to various concentrations of solution phase hydrogen peroxide in the presence of $I^-$ and $Mo^{(VI)}$ at 20° C.

Biospecific responses result from linking the chemoresistive device with the biorecognition reaction of a biologically active molecule. The simplest demonstrable case is that for an oxidoreductase enzyme such as glucose oxidase which produces hydrogen peroxide and hence elicits a chemical response similar to that described preceding. The direct reaction of hydrogen peroxide with polypyrrole and polyacetylene has been found to favor chemical oxidation over charge transfer reaction. For this reason mediation is found to be necessary. FIG. 12, Scheme II, shows the approach used by Umana and Waller (1986) and applied here to chemoresistive signal detection.

I this scheme hydrogen peroxide reacts with iodide in the Mo$^{(VI)}$ catalyzed generation of iodine. Iodine then reacts with the polypyrrole film effecting an increase in its electrical conductivity. In this scheme the polypyrrole is a direct participant to transduction as its electrical properties are indirectly modulated by redox charge transfer with the analyte of interest. Test solutions were prepared to $10^{-2}$M I$^-$ and $10^{-3}$M M Mo$^{(VI)}$ in 2 ml volumes of pH 6.0 phosphate buffer. Incremental additions of hydrogen peroxide produced the calibration plot shown in FIG. 10.

The chemoresistive system PPy/PVAVS is seen to be capable of detecting hydrogen peroxide down to $10^{-4}$M with good sensitivity. This system could therefore be used to detect the non-redox-active molecule glucose through the biorecognition reaction of the enzyme glucose oxidase.

EXAMPLE 7

The Glucose Biosensor

Glucose oxidase is a very stable, structurally rigid glycoprotein with an approximate globular diameter of ca. 86 A (Nakamura, et. al., 1976). The two redox active Flavin Adenine Dinucleotide (FAD/FADH2) centers of the enzyme are located deep within the glycoprotein shell (Worthington Manual, 1977). For this reason, direct charge transfer between these redox centers and the redox active polymer films of the current biosensor devices is not possible (Heller and Degani, 1987). However, use can be made of the reactions which serve to couple the biorecognition reaction of the enzyme with the biospecific hydrogen peroxide response described preceding.

Figure 11:
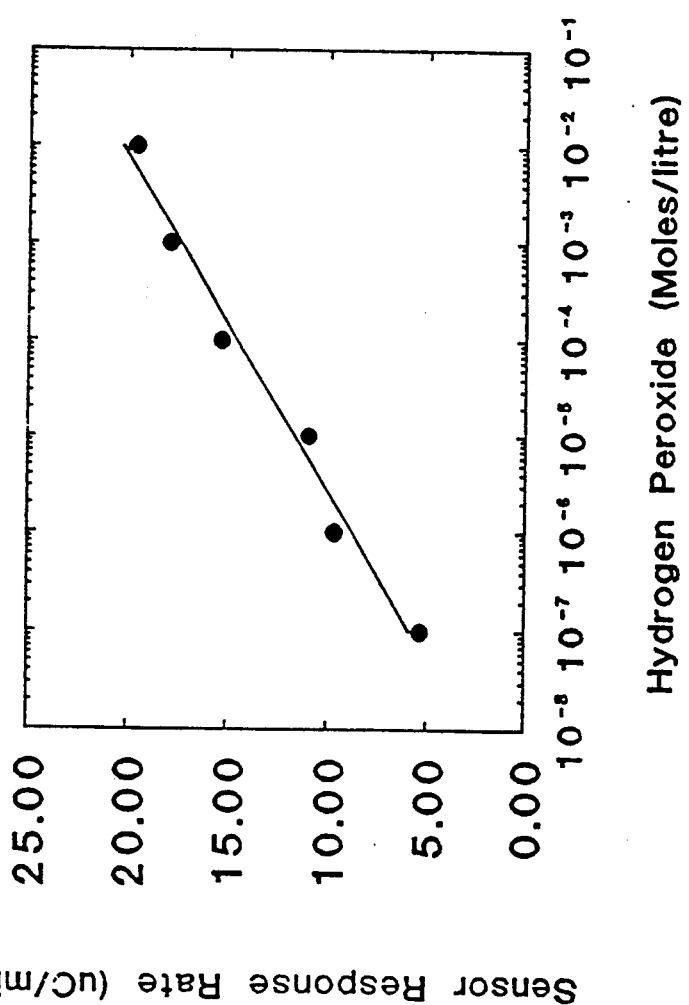
FIG. 11 is a graph showing the kinetic chemoresistive responses of the polyaniline-based sensor illustrated in FIG. 9 to various concentrations of hydrogen peroxide in 0.2M HCl.
Figure 14:
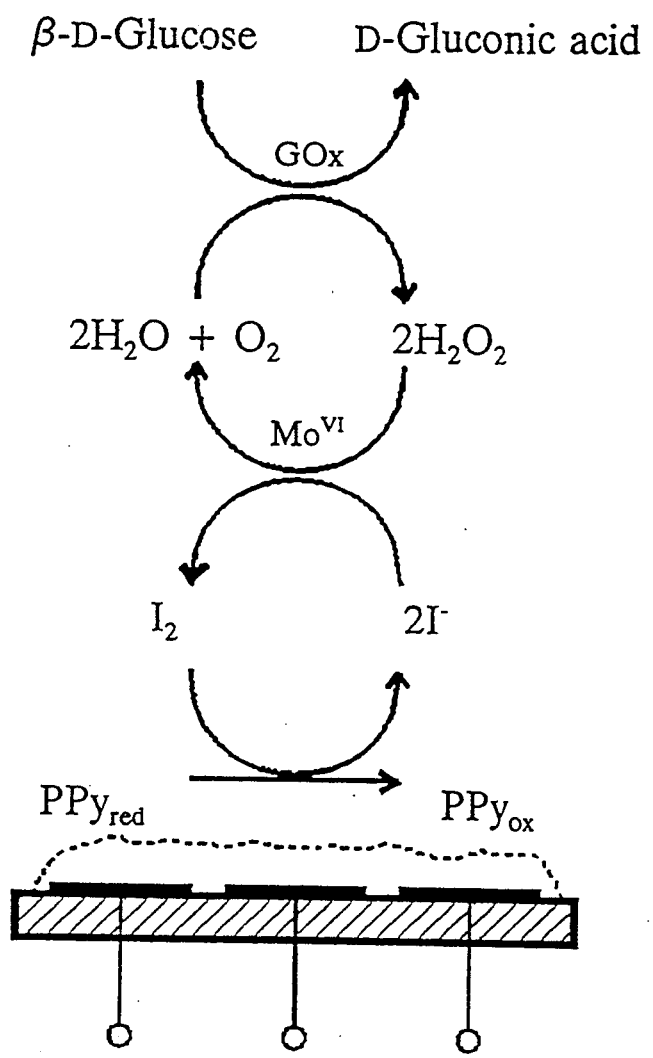
FIG. 14 is an illustration of a typical mediated biosensor reaction, SCHEME 3.
Figure 15:
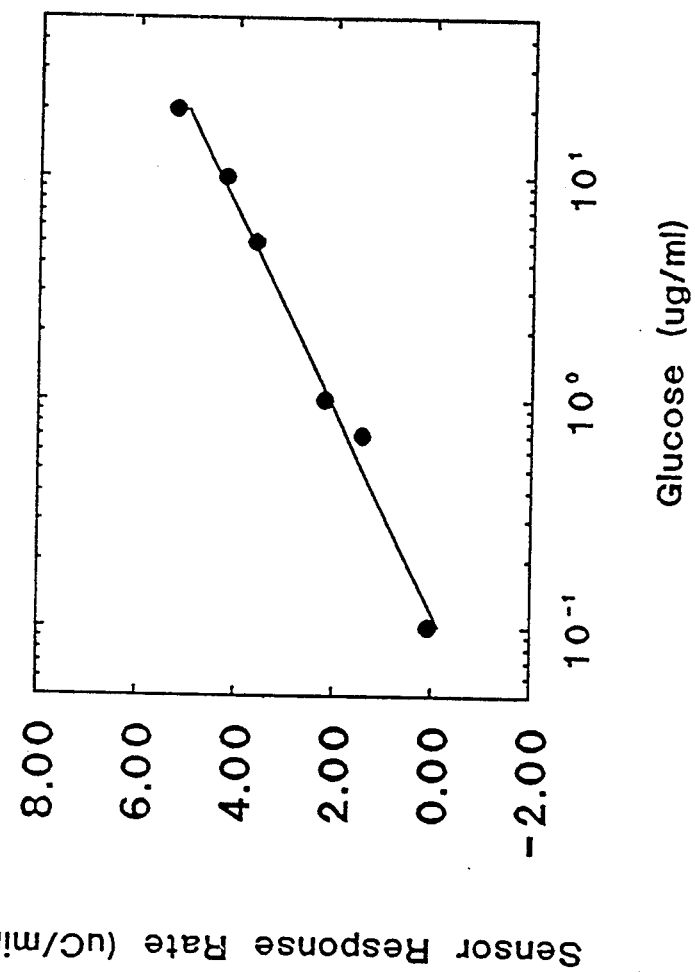
FIG. 15 is a graph showing the kinetic dose/response curve for the chemoresistive glucose biosensor based on the system (PPy/PVAVS/GOx) for variations in glucose concentration over the range 0.1 to 20 µg/ml in pH 6.0, 0.1M phosphate buffered potassium chloride a 20° C.

As shown in FIG. 14, Scheme III, glucose oxidase readily oxidizes glucose to gluconic acid while the redox active FAD cofactor is reduced to FADH$^2$. Under aerobic conditions the FAD is regenerated by solution phase, diffusible, molecular dioxygen which is itself reduced to hydrogen peroxide. In the current biosensor device, the hydrogen peroxide is nascently produced within the polymer matrix where it, oxidizes the electroactive polymer from its initialized or reduced redox composition to a more conducting redox composition. The dynamically changing chemoresistance of the device is followed as described previously. Biospecific chemoresistive responses of glucose biosensors formed from electroactive polypyrrole and conferred with the biospecificity of the enzyme glucose oxidase (PPy/PVAVS/GOx) were obtained for films initialized at $-250$ mV vs Ag/AgCl,3MCl$^-$ for 60 sec followed by interrogation with a 10 mV pulse potential of pulse width of 50ms and rest period of 500 ms. The responses show an initial quiescent period (corresponding to the blank or background response) prior to addition of the substrate dose. Addition of the substrate is followed by a further brief induction period then by rapid change in the device chemoresistance. Response saturation occurs after about two minutes. The kinetic response taken as the initial rate of change of chemoresistance following dose addition was measured for various glucose concentrations over the range of 0.1 to 20.0 mg/1 and is presented in FIG. 11 as a calibration plot. A linear relationship was observed between the initial rate and the logarithm of the glucose concentration in the range 0.1 to 20 μg/ml glucose.

Glucose biosensor probes prepared in the above manner were found to be stable for up to six weeks when stored at 5° C. in pH 6.0 phosphate buffered potassium chloride. The leaching of GOx from the membrane film appears to be the major source of reduced activity. Methods to specifically immobilize the enzyme are being developed.

While the present invention has been described with reference to the enclosed Figures and detailed description, it is to be appreciated that other embodiments fulfill the spirit and scope of the present invention, and that the true nature and scope of the present invention is to be determined with reference to the claims appended hereto.

I claim:

1. An analytical method for measuring an analyte that uses the interrogration of chemoresistive sensor responses from electroactive polymer films, said method using an electroactive polymer sensor device and comprising the following steps:
   (a) measuring open circuit electrical potential an electroactive polymer film of said device;
   (b) applying a potentiostatic electrical potential relative to a reference electrode to said polymer film which oxidizes or reduces said polymer film to provide an initial reduced or oxidized state, and thereby provides said polymer film with an initial electrical resistance;
   (c) measuring the electrical resistance of the polymer film resulting from (b) by applying to the polymer film a non-perturbating voltage pulse, removing the voltage pulse from the polymer film for a period following the pulse duration, making a potentiometric measurement of the open circuit potential of the polymer film and applying to the polymer film a subsequent non-perturbating voltage pulse relative to the measured open circuit potential before said polymer film reacts with an analyte to which it has been made specific;
   (d) reacting said polymer film with an analyte, to which it has been made specific whereby the reaction causes a change in electrical resistance of said polymer film;
   (e) measuring the electrical resistance of the polymer film resulting from (d) by applying to the polymer film a non-perturbating voltage pulse, removing the voltage pulse from the polymer film for a period following the pulse duration, making a potentiometric measurement of the open circuit potential of the polymer film and applying to the polymer film a subsequent non-perturbating voltage pulse relative to the emasured open circuit potential while said polymer film reacts with an analyte to which it has been made specific; and
   (f) determining the rate of change of the electrical resistance and total amount of change of the electrical resistance from which the concentration of the analyte is determined.

2. The method of claim 1 wherein said electrical resistance measurement of the polymer film of said device is made by the following steps repeated in sequence;
   (a) applying to the polymer film a non-perturbating voltage pulse in the range of plus or minus 5 to 25 millivolts for a specified pulse duration of between about 1 and 100 milliseconds;
   (b) removing the voltage from the polymer film for a period following the pulse duration, the duration of said period being about 10 times the duration of the applied pulse;
   (c) making a potentiometric measurement of the open circuit potential of the polymer film; and
   (d) applying to the polymer film a subsequent non-perturbating voltage pulse relative to the measured open-circuit potential.

3. The method of claim 2 wherein said steps (a)-(d) are repeated.

* * * * *